(12) United States Patent
Schiller et al.

(10) Patent No.: US 12,016,827 B2
(45) Date of Patent: *Jun. 25, 2024

(54) PROCESS FOR THE MANUFACTURE OF A SOLID PHARMACEUTICAL ADMINISTRATION FORM

(71) Applicant: Merck Patent GmbH, Darmstadt (DE)

(72) Inventors: Stefan Schiller, Darmstadt (DE); Andrea Hanefeld, Darmstadt (DE); Gerhard Jonschker, Heppenheim (DE)

(73) Assignee: MERCK PATENT GMBH, Darmstadt (DE)

( * ) Notice: Subject to any disclaimer, the term of this patent is extended or adjusted under 35 U.S.C. 154(b) by 15 days.

This patent is subject to a terminal disclaimer.

(21) Appl. No.: 17/559,215

(22) Filed: Dec. 22, 2021

(65) Prior Publication Data

US 2022/0110830 A1  Apr. 14, 2022

Related U.S. Application Data

(62) Division of application No. 16/331,554, filed as application No. PCT/EP2017/072551 on Sep. 8, 2017, now Pat. No. 11,229,577.

(30) Foreign Application Priority Data

Sep. 9, 2016  (EP) ..................................... 16188177

(51) Int. Cl.
*B29C 64/165* (2017.01)
*A61J 3/10* (2006.01)
(Continued)

(52) U.S. Cl.
CPC ............... *A61J 3/10* (2013.01); *A61K 9/2095* (2013.01); *B29C 64/165* (2017.08);
(Continued)

(58) Field of Classification Search
CPC ........ A61J 3/10; A61K 9/2095; B29C 64/165; B29C 64/209; B29C 64/264; B29C 64/30;
(Continued)

(56) References Cited

U.S. PATENT DOCUMENTS 9,339,489 B2 * 5/2016 Jacob ................... A61K 9/7007
9,643,359 B2 * 5/2017 Baumann ................ B22F 12/41
(Continued)

FOREIGN PATENT DOCUMENTS

CN  1976799 A  6/2007
CN  105034360 A  11/2015
(Continued)

OTHER PUBLICATIONS

Alhnan et al. "Emergence of 3D Printed Dosage Forms: Opportunities and Challenges" Pharmaceutical Research_2016_ 33_ 1817-1832.
(Continued)

*Primary Examiner* — Nahida Sultana
(74) *Attorney, Agent, or Firm* — MILLEN, WHITE, ZELANO & BRANIGAN, P.C.; Csaba Henter

(57) ABSTRACT

The present invention relates to a process for the preparation of a solid pharmaceutical administration form using a 3D printing process as well. The process is a printing process that allows the production of solid pharmaceutical administration forms in a flexible manner and in conformity with the high quality standards required for the production of pharmaceuticals.

7 Claims, 7 Drawing Sheets

(51) Int. Cl.
*A61K 9/20* (2006.01)
*B29C 64/209* (2017.01)
*B33Y 10/00* (2015.01)
*B33Y 80/00* (2015.01)
*B29L 31/00* (2006.01)
*B33Y 30/00* (2015.01)

(52) U.S. Cl.
CPC ............ *B29C 64/209* (2017.08); *B33Y 10/00* (2014.12); *B33Y 80/00* (2014.12); *B29L 2031/753* (2013.01); *B33Y 30/00* (2014.12)

(58) Field of Classification Search
CPC ......... B33Y 10/00; B33Y 80/00; B33Y 30/00; B33Y 40/00; B29L 2031/753
See application file for complete search history.

(56) References Cited

U.S. PATENT DOCUMENTS

| | | | |
|---|---|---|---|
| 9,669,009 | B2 | 6/2017 | Jacob et al. |
| 9,944,020 | B2 | 4/2018 | Lechmann et al. |
| 10,265,910 | B2 | 4/2019 | Giller |
| 10,357,918 | B2 | 7/2019 | Giller |
| 11,229,577 | B2 * | 1/2022 | Schiller .................. B33Y 80/00 |
| 2004/0062804 | A1 | 4/2004 | Lee et al. |
| 2006/0030000 | A1 | 2/2006 | Alitalo et al. |
| 2007/0183918 | A1 | 8/2007 | Monsheimer et al. |
| 2007/0243257 | A1 | 10/2007 | Bedos et al. |
| 2015/0210010 | A1 | 7/2015 | Napadensky |
| 2017/0095596 | A1 | 4/2017 | Petrak et al. |
| 2017/0239889 | A1 * | 8/2017 | Ganapathiappan .... B33Y 10/00 |
| 2018/0147153 | A1 | 5/2018 | McNally |
| 2019/0125666 | A1 * | 5/2019 | Okushima ............... A61K 47/26 |
| 2019/0125681 | A1 | 5/2019 | Albed Alhnan |

FOREIGN PATENT DOCUMENTS

| | | | |
|---|---|---|---|
| KR | 20060123637 | A | 12/2006 |
| WO | 12058278 | A2 | 5/2012 |
| WO | 14144512 | A1 | 9/2014 |
| WO | 15143553 | A1 | 10/2015 |

OTHER PUBLICATIONS

Deng Guang Yu Et Al: "Three-dimensional Printing in Pharmaceutics: Promises and Problems" Journal of Pharmaceutical Sciences, vol. 97, No. 9, Sep. 1, 2008 (Sep. 1, 2008), pp. 3666-3690, XP055423076, ISSN: 0022-3549.

Fina Fabrizio Et Al: "Selective Laser Sintering (sls) 3d Printing of Medicines" International Journal of Pharmaceutics, Elsevier, Amsterdam, NL, vol. 529, No. 1, Jun. 29, 2017 (Jun. 29, 2017), pp. 285-293, XP085156673, ISSN: 0378-5173.

Goyanes A. Et Al.: "Fused-filament 3d Printing (3dp) for Fabrication of Tablets International" J Pharm, vol. 476, 2014, pp. 88-92.

Katstra W.e. Et Al.: "Oral Dosage Forms Fabricated by Three Dimensional Printing" J Contr Rel, vol. 66, 2000, pp. 1-9.

Khaled S.a. Et Al.: "Desktop 3d Printing of Controlled Release Pharmaceutical Bilayer Tablets" Int J Pharm, vol. 461, 2014, pp. 105-111.

Seyed Farid Seyed Shirazi Et Al: "A Review on Powder-based Additive Manufacturing for Tissue Engineering: Selective Laser Sintering and Inkjet 3d Printing" Science and Technology of Advanced Materials, vol. 16, No. 3, Jun. 20, 2015 (Jun. 20, 2015), pp. 033502, XP055414960, ISSN: 1468-6996.

International Search Report PCT/EP2017/072551 dated Dec. 15, 2017 (pp. 1-3).

English translation of office Action in corresponding Korean Patent application 2019-7009623 dated Jun. 22, 2023 (pp. 1-10).

* cited by examiner

Figure 6:
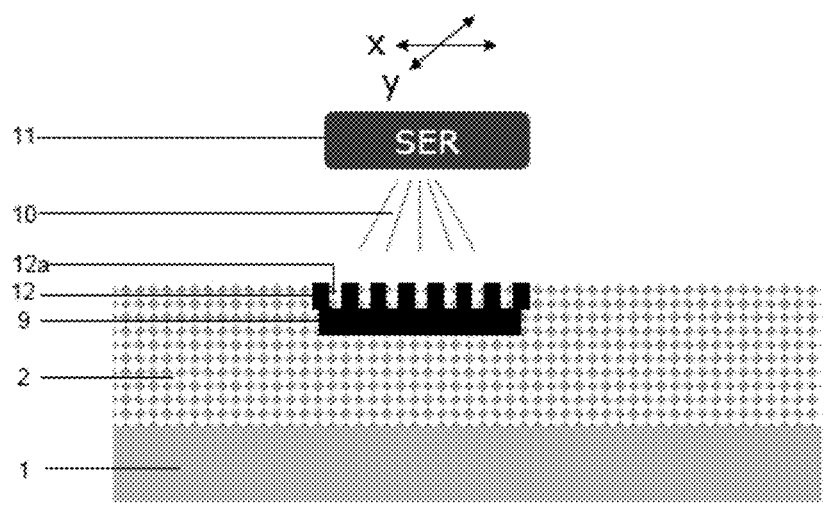

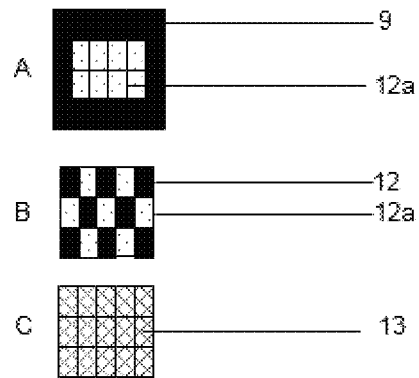
Figure 6 A,B,C
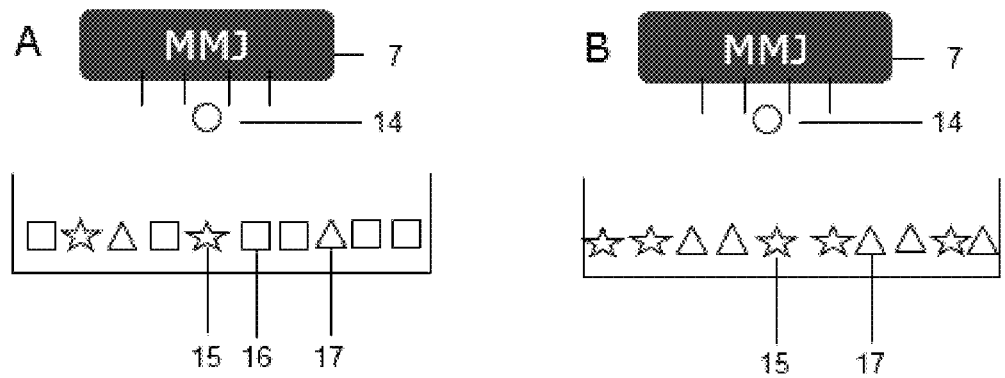
Figure 7 A,B

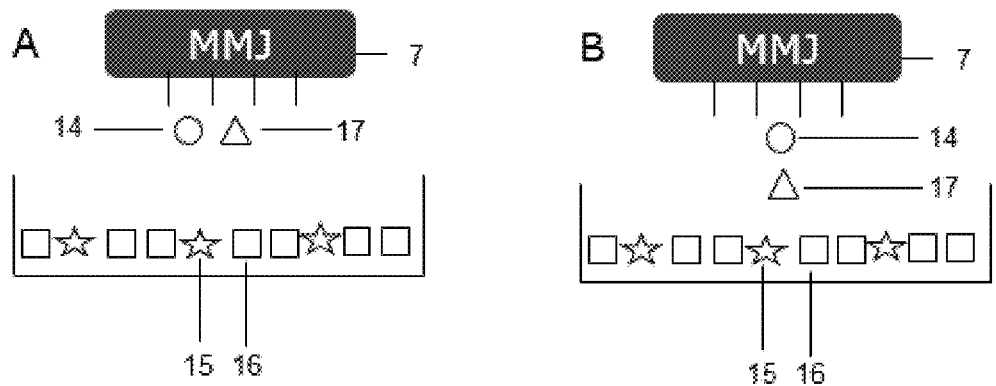
Figure 8 A,B
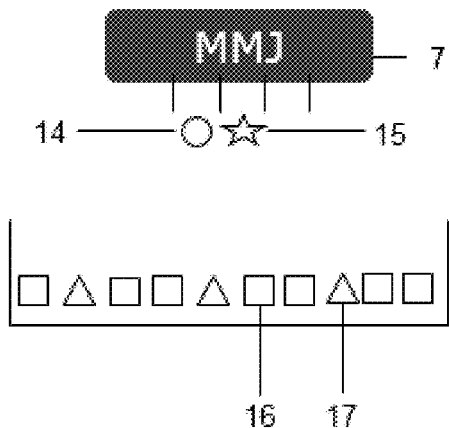
Figure 9

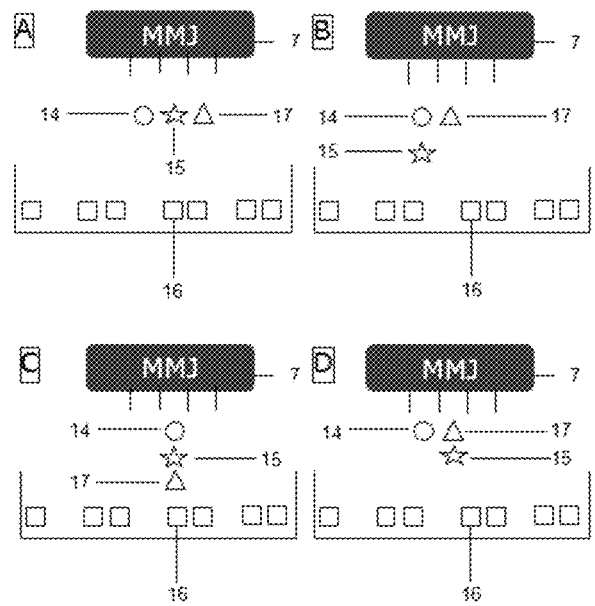
Figure 10 A,B,C,D
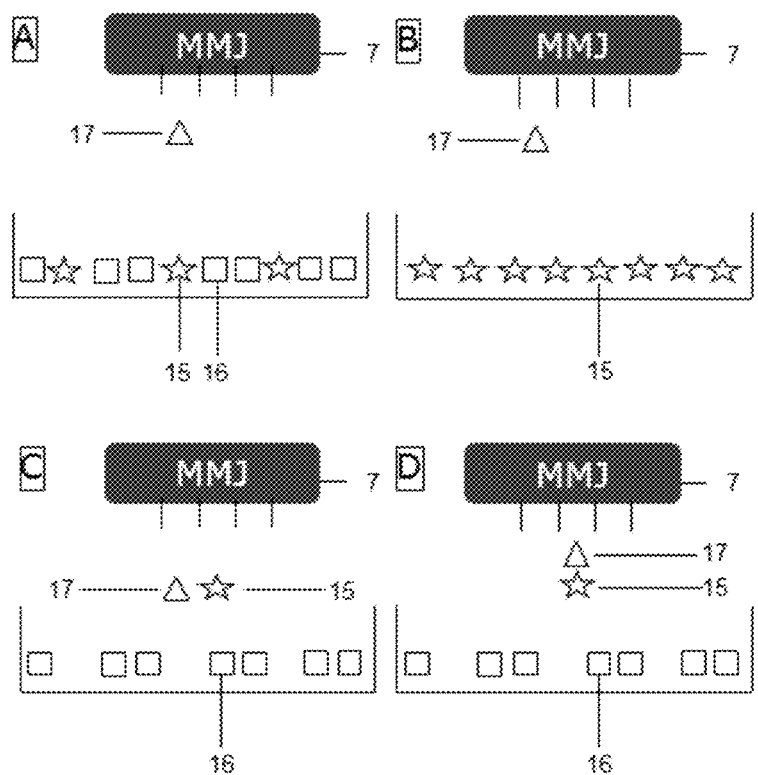
Figure 11 A,B,C,D

PROCESS FOR THE MANUFACTURE OF A SOLID PHARMACEUTICAL ADMINISTRATION FORM

The present invention relates to a process for the preparation of a solid pharmaceutical administration form using a 3D printing process as well. The process is a printing process that allows the production of solid pharmaceutical administration forms in a flexible manner and in conformity with the high quality standards required for the production of pharmaceuticals.

It is believed that future improvements in disease treatment is driven by point-of-care and home-based diagnostics linked with genetic testing and emerging technologies such as proteomics and metabolomics analysis. This has led to the concept of personalized medicine, which foresees the customization of healthcare to an individual patient.

Medication can be applied to the patient by using different pharmaceutical formulations that are adapted to the desired application method, for example to oral (including buccal or sublingual), rectal, nasal, topical (including buccal, sublingual or transdermal), vaginal or parenteral (including subcutaneous, intramuscular, intravenous or intradermal) application. In general, oral application is preferred as such application is easy and convenient and does not cause any harm that may be associated with other application methods such as parenteral application.

Pharmaceutical formulations usable for oral administration are, for example, capsules or tablets; powders or granules; solutions or suspensions in aqueous or non-aqueous liquids; edible foams or foam foods; or oil-in-water liquid emulsions or water-in-oil liquid emulsions.

Tablets for oral administration are by far the most common dosage form, and are generally prepared by either single or multiple compressions (and in certain cases with moulding) processes. Tablets are usually prepared by using multiple process steps such as milling, sieving, mixing and granulation (dry and wet). Each one of these steps can introduce difficulties in the manufacture of a medicine (e.g., drug degradation and form change), leading to possible batch failures and problems in optimization of formulations.

Tablets are almost universally manufactured at large centralized plants via these processes using tablet presses essentially unchanged in concept for well over a century. This route to manufacture is clearly unsuited to personalized medicine and in addition provides stringent restrictions on the complexity achievable in the dosage form (e.g., multiple release profiles and geometries) and requires the development of dosage forms with proven long-term stability.

Use of 3D printing technology was proposed as an alternative approach to provide dosage forms as this potentially allows manufacture of personalized medicines at the point of care (Khaled S. A. et al.: Desktop 3D printing of controlled release pharmaceutical bilayer tablets, Int J Pharm 461 (2014) 105-111). Khaled et al. describes the printing of guaifenesin tablets by using an extrusion based 3D printer. According to this method a water based HPMC gel is prepared, filled into the printer head of an extrusion based 3D printer and printed. In such printing process a multitude of layers are placed successively on top of each other thereby forming the tablet. However, use of a gel like HPMC gel to prepare tablets is only feasible with active pharmaceutical ingredients (APIs) that are compatible with and stable in aqueous environment. Further, the solvent, especially the water that is present in the gel, has to be removed after printing which slows down the process flow. In addition, change of manufacturing from a tablet having as specific API to a different tablet with a different API requires extensive cleaning operations and extends setup times, especially as such manufacturing process has to meet the high quality standards (Good Manufacturing Practice (GMP)) that are compulsory in the manufacturing of medicinal products.

Katstra W. E. et al. discloses 3D printing of a tablet using a so-called solid freeform fabrication (SFF) technique which employs powder processing wherein the tablet is build-up in a layer-wise manner (Katstra W. E. et al.: Oral dosage forms fabricated by Three Dimensional Printing, J Contr Rel 66 (2000) 1-9). The process uses a 3D printer composed of a pair of horizontal X-Y axes that are suspended over a vertical piston, providing control over three directions of motion. For manufacture of tablet a thin layer of powder is spread onto a piston plate, droplets of a liquid binder solution are distributed over the powder bed through a nozzle that is moved back and forth and which provides binding of the powder particles together and generation of a 2D pattern. After lowering the piston by a fixed distance, another thin layer of powder is spread, and the process is repeated. The process described by Katstra et al. also requires a drying step to remove the liquid that has entered the formulation by the addition of binder solution which slows down the process flow. Further, the mechanical properties of the solid dosage forms, such as friability, might be critical in view of that the particles of the powder contained therein are only attached to each other by means of a binder and no compression step as it is used in conventional tableting processes is involved. In addition, change of manufacturing from a tablet having as specific active pharmaceutical ingredient (API) to a different tablet with a different API requires extensive cleaning operations to avoid cross contamination, especially in view of the formation of dust. To fulfill the compulsory high quality standards (Good Manufacturing Practice (GMP)) extended setup times are associated with such process.

Goyanes A. et al. describes 3D extrusion printing of a tablet using drug loaded into a polymer (Goyanes A. et al.: Fused-filament 3D printing (3DP) for fabrication of tablets International, J Pharm 476 (2014) 88-92). In such method extruded filaments of polyvinyl alcohol (PVA) are loaded with fluorescein sodium as model drug by incubation in an ethanolic fluorescein solution for 24 hours, dried in an oven and subsequently melt extruded in a 3D printer at 220° C. However, the loading of PVA with API is time consuming, limits its applicability for APIs with different physicochemical properties and does not allow preparation of filaments with high contents of API and finally no tablets with high drug content. In fact, the diffusion driven loading step requires that the API must fulfill specific properties in terms of solubility and molecular size to be a suitable subject for such process. Further, the API must have a good thermal stability to be not destroyed at the high extrusion temperature (220° C.). As a result such process is applicable to a very limited number of APIs only, which are applied to the patient in low doses and that meet the very specific physicochemical properties described above.

WO 2014/188079 discloses manufacturing of oral dosage forms of vitamin(s) and/or dietary mineral(s) or nicotine by inkjet printing. APIs are dissolved in mixtures of water and alcohols (propylene glycol, glycerol, ethanol), filtered and printed in squares of 1 cm×1 cm on paper using an inkjet printer. However, such dosage forms are rather two dimensional which is difficult to be handled by and administrated to the patient compared to three dimensional tablets. Further, due to the low mass of the dosage form, only dosage forms that contain very low dosages can be produced. In addition, the APIs must be soluble and stable in water/alcohol solutions.

All 3D printing processes that are described for the preparation of tablets and that are in principle usable for decentralized production of personalized solid dosage forms exhibit several disadvantages that hinder their broad applicability. Therefore, there is a strong demand for a process that overcomes such disadvantages. Especially a process is needed that is fast, that is applicable to a broad range of APIs in terms of their physicochemical properties and that is applicable also to APIs that are administrated to the patient in high dosage ranges (hundreds of milligrams to grams).

A process that meets such criteria is made available by the present invention.

The present invention is directed to a process for the manufacture of a solid pharmaceutical administration form comprising an active ingredient comprising the steps
  (a) spreading a powder comprising a fusible material and an active ingredient across the manufacturing area to create a powder bed;
  (b) jet printing a fluid comprising an energy absorbing material onto the powder;
  (c) irradiating the powder to induce heating of the energy absorbing material in the powder and thereby to induce melting and fusing of the fusible material present in the powder;
  (d) spreading a layer of powder onto the surface of unfused and fused powder and subsequently performing step (b) and step (c);
  (e) repeating step (d) as often as needed to build up the solid pharmaceutical administration form;
  (f) separating the solid pharmaceutical administration form from the powder bed.

The process can be run on a 3D printer composed of a pair of horizontal X-Y axes that are suspended over a vertical piston, providing control over three directions of motion and that is equipped with jet head as known from ink jet printing technology. Preferably the jet head comprises a multichannel nozzle that allows printing of multiple fluids successively or in parallel. For manufacture of solid pharmaceutical dosage form is spread onto a mounting plate to create a powder bed, the fluid is precisely distributed over predefined areas of the powder bed through a jet head that is moved over the powder bed. By irradiation of the powder bed the fusible material is at least partially fused thereby generating a 2D pattern. After lowering the mounting plate by a fixed distance, a layer of powder is spread, and the process is repeated. Instead of lowering the mounting plate the spreading means can be raised by a fixed distance.

The term "solid pharmaceutical administration form" as used herein means any pharmaceutical formulation that is solid and provides a dosage unit of an active pharmaceutical ingredient that can be administered to a patient by any way of application such as oral, rectal, vaginal, implantation. The solid pharmaceutical administration form can have any shape adapted to the application requirements, e.g. round, oval, rod like, torpedo shaped etc. Examples of solid pharmaceutical administration forms are tablets, pills, caplets, suppositories, implants.

The term "active ingredient" as used herein means any ingredient that provides a pharmacological or biological effect when applied to a biological system. The active ingredient may be a pharmaceutical drug, biological matter of viral or ling origin. Examples of an active ingredient that may be used in the process of the present inventions are insulin, heparin, calcitonin, hydrocortisone, prednisone, budesonide, methotrexate, mesalazine, sulfasalazine, amphotericin B, nucleic acids, or antigens (peptides, proteins, sugars, or other substances that form surfaces recognized by the immune system, either produced, extracted, or homogenized from tissue, an organism or a virus).

The term "spreading" as used herein means a process where a planar layer of powder is applied to a planar ground. Spreading of powder can be achieved by using means that are suitable to create a planar layer of powder. Examples of such means are a doctor blade or a roller that can be moved in parallel to planar ground such as a mounting area or an existing powder layer to distribute the powder from a reservoir across the planar ground. By the use of a roller a certain level of compaction can be obtained, which may be advantageous for the manufacture of the solid pharmaceutical dosage form.

The term "fusible material" is a material that melts and fuses upon heating. The fusible material has a rather low melting point or glass transition temperature to keep the operation temperature low and to keep potential detrimental effects on the solid pharmaceutical dosage form, especially the active ingredient, as low as possible but it has to be high enough to assure stability of the shape of the solid pharmaceutical dosage form under usual storage conditions, e.g. room temperature. Preferably, the glass transition temperature would be at least 20° C. higher than the projected storage condition at the same humidity. A suitable range of melting points or glass transition temperatures would be 50-150° C., more preferably 50-100° C., most preferably 60-80° C. Examples of fusible materials are lipids, incl. fats and waxes, derivatives thereof; resins; low melting sugars and sugar alcohols, incl. fructose, sorbitol, xylitol; mixtures of these to reduce melting point; modified sugars such as sucrose esters, sorbitan esters; vitamin E TPGS; pharmaceutical polymers with or without plasticizer (incl. water) with sufficiently low melting point or glass transition temperature, incl. PEG/PEO, PEO esters and ethers, PVAc, PVP, PCL, Poloxamers, PVPVA, celluloses and derivatives thereof, poly-acrylates, poly-methacrylates, PLA, PLGA, gelatin, alginate, shellac, agar; composites, mixtures and blends thereof.

As used herein, "fusing" means complete fusing or partial fusing. As used herein "melting" means complete or partial melting.

As used herein, "a" or "an" shall mean one or more. As used herein when used in conjunction with the word "comprising," the words "a" or "an" mean one or more than one. As used herein "another" means at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−1-3% of the recited value) that one of ordinary skill in the art would consider equivalent to the recited value (e.g., having the same function or result). In some instances, the term "about" may include numerical values that are rounded to the nearest significant figure.

As used herein, "jet printing" refers to a process where a fluid is distributed to the powder bed by ejecting droplets of fluid at high speed towards and onto the powder bed. Ejection of droplets can be performed with utmost precision to predefined target place. By managing size of droplets, amount of droplets and specific target place the exact placement on and penetration depth in a substrate can be precisely controlled. Jet printing is well-known from inkjet printing technology but in contrast to this technology the fluid that is printed in the process of the present invention is not an ink for printing of images but a fluid that contains materials that are usable for printing of solid pharmaceutical administration forms, especially an energy absorbing or reflecting material, a fusible material or an active ingredient.

The fluid used for jet printing is a liquid wherein the material to be printed is distributed. Examples of liquids that can be used for distribution of the material are water, organic solvents, such as ethanol, or mixtures of both, whereby the organic solvent may be soluble with one another or not. The material may be dissolved, suspended or emulsified in the fluid. Auxiliaries such as surfactants may be used, e.g. to improve dispersibility of the material in the fluid and/or spreading or wetting of particles in the powder bed.

The term "energy absorbing material" as used herein means any material that absorbs IR, NIR, VIS, UV or microwave irradiation and converts it to some extend to heat. In principle, any energy absorbing material can be used in the present invention. Energy absorbing materials that are especially suitable for the present invention are carbon black, pigments and anorganic salts, e.g. oxides and salts and alloys of iron, zinc, magnesium, aluminium or other metals, organic dyes and liquids (e.g. water). Certain energy absorbing materials may further possess the property to reflect or scatter radiation, which may lead to an improved heat distribution. Examples may include pigments of a certain particle shape and size, pigments with layered structures and interference pigments such as composites comprising silicate minerals (such as sheet silicate (phyllosilicate) minerals (mica) or potassium aluminium silicate) and oxides of titanium or iron (Candurin® pigments). The energy absorbing material can be used in any form and particle size that is processable and that provides heat generation and distribution suitable for running the process. The energy absorbing material can have any particle size that is suitable to be processed in the process and that is suitable to create the heat needed. For example, the energy absorbing material can have a mean particle diameter from about 10 nm to about 200 µm. When jetting the energy absorbing material, the preferred mean particle diameter can be about 10 nm to about 10 µm, preferably from about 50 nm to about 5 µm, more preferably from about 100 nm to about 2 µm. When including the energy absorbing material in the powder, the preferred mean particle diameter can be about 1 µm to about 200 µm, preferably from about 10 µm to about 100 µm, more preferably from about 30 µm to about 70 µm.

The process as described above uses an energy absorbing material to provide the heat that is necessary for melting and fusing of the fusible material. However, depending on the melting point or glass transition temperature of the fusible material, the absorption spectrum of components of the powder bed and the amount of thermal energy provided by the irradiation, the irradiation alone can be sufficient to induce melting and fusing of the fusible material so that the addition of an energy absorbing material is not necessary. In this case jet printing of an energy absorbing material can be replaced by jet printing of the fusible material.

Therefore, the present invention is also directed to a process for the manufacture of a solid pharmaceutical administration form comprising an active ingredient comprising the steps
  (a) spreading a powder comprising an active ingredient across the manufacturing area to create a powder bed;
  (b) jet printing a fluid comprising a fusible material onto the powder;
  (c) irradiating the powder to induce melting and fusing of the fusible material present in the powder;
  (d) spreading a layer of powder onto the surface of unfused and fused powder and subsequently performing step (b) and step (c);
  (e) repeating step (d) as often as needed to build up the solid pharmaceutical administration form;
  (f) separating the solid pharmaceutical administration form from the powder bed.

In some instances, the processes described above may lead to so much heat development that direct removal of the solid pharmaceutical dosage form from the powder bed after its manufacture causes damage of the solid pharmaceutical dosage form, especially damage of its shape. In this case a cooling step is introduced between manufacturing of the solid pharmaceutical dosage form and its removal from the mounting plate. Accordingly, the invention is also directed to a process for the manufacture of a solid pharmaceutical administration form as set forth above, that is characterized in that a cooling step is introduced between steps (d) and (e).

The cooling step comprises any method that leads to sufficient reduction of the temperature of the solid pharmaceutical form to a temperature value to assure that the shape of the solid pharmaceutical dosage for is maintained when it is removed from the mounting plate. Examples of a cooling step are simple remaining of the solid pharmaceutical dosage form on the mounting plate at ambient temperature until obtaining sufficient temperature reduction or active cooling, such as cooling by a cold air flow. Preferably, the cooling step would allow to control the cooling rate and thus the physical characteristics of the quenched melt.

In some instances, the processes described above may lead to physical changes such as melting of the fusible material in places adjacent to the intended region. Especially processes using materials with broader melting or glass transition ranges or strong heat dissipation may be affected by this phenomenon. Such processes may be improved by selectively cooling of the fusible material in places adjacent to the intended region. Such improvement may be achieved by using a parting agent. As used herein a "parting agent" refers to an agent that facilitates the shape and removal of the object of fused powder created by the irradiation by minimizing or avoiding sticking of powder of the surrounding powder bed to the object. Minimizing or avoiding of powder sticking to the object can be achieved by selective cooling of the surrounding powder bed, preferably by evaporation cooling. Agents that may be used as parting agent comprise volatile fluids, preferably pharmaceutically acceptable solvents such as water, methanol or ethanol, liquid alkanes such as pentane, hexane or heptane, more preferably water or ethanol.

By precise placement of the parting agent to the intended edges in the powder bed shape accuracy and edge definition of the printed object can be improved. The parting agent may further serve as means to modulate surface or matrix porosity of the resulting dosage form.

In the process of the present invention precise placement of the parting agent can be easily realized by jet printing of the parting agent onto the powder, either in parallel or subsequently in step (b). Accordingly, the invention is also directed to the process for the manufacture of a solid pharmaceutical administration form as set forth above, wherein in step (b) a parting agent is jet printed onto the powder in parallel or subsequently.

In some instances, especially if an active ingredient has a rather low melting point or glass transition temperature that is comparable to the fusible material, for example, if it has a glass transition temperature of at least 20° C. higher than the projected storage condition at the same humidity, and/or if an active ingredient has energy absorbing properties comparable to the energy absorbing material, it may be feasible that a solid pharmaceutical administration form can be formed by the process of the invention without the presence of a fusible material or an energy absorbing material. In such instances the process of the present invention can be run without the presence of a fusing material in step (a) or adding a fusible material by jet printing (step b). Accordingly, the present invention is further directed to a process for the manufacture of a solid pharmaceutical administration form comprising an active ingredient comprising the steps (a) spreading a powder comprising an active ingredient across the manufacturing area to create a powder bed;
(c) irradiating the powder to induce melting and fusing of the fusible material present in the powder;
(d) spreading a layer of powder onto the surface of unfused and fused powder and subsequently performing step (b) and step (c);
(e) repeating step (d) as often as needed to build up the solid pharmaceutical administration form;
(f) separating the solid pharmaceutical administration form from the powder bed.

In some instances, the speed of the processes described above may be improved by pre-heating the build chamber, the powder bed or powder supply with a suitable method without disrupting the powder bed. The powder may be heated to a temperature 2-50° C. below the melting point or glass transition temperature of the fusible material at which the powder bed still retains favorable flow properties. Accordingly, the invention is also directed to a process for the manufacture of a solid pharmaceutical administration form as set forth above, wherein pre-heating is applied in steps (a) and (d) prior to or after spreading the powder.

The shape of the solid pharmaceutical dosage form can be easily determined by controlling the area of jet printing of either the energy absorbing material or the fusible material to the powder bed. Upon irradiation in the first case the energy absorbing material heats up resulting in melting and fusing of the fusible material surrounding the energy absorbing material and thereby forming a fused three-dimensional network layer. In the second case irradiation directly heats up the fusible material resulting in melting and fusing of the fusible material thereby causing a fused three-dimensional network layer.

Any desired shape, such as rectangular, quadratic, cruciform, circular, ring (donut) or oval, can be achieved by operating the processes. By assembling drug containing layers with different shapes solid pharmaceutical administration forms of any three-dimensional shape can be easily obtained. Compared to conventional tablet production the process of the present invention provides wide flexibility with respect to the shape the solid pharmaceutical administration form. Advantageously the shape of the solid pharmaceutical administration form can be easily adapted to various specific demands and, in addition, allows new shapes that cannot be made available by conventional tablet manufacturing processes, such as, for example, a capsule filled with solid powder.

The process of the invention can provide solid pharmaceutical administration forms with different dosages and/or different active ingredients in a flexible manner. For example solid pharmaceutical administration forms with different dosages but the same active ingredient can be manufactured by simply controlling the number of API containing layers that are attached to one another. Solid pharmaceutical administration forms with the same active ingredient but different release properties such as an administration form, wherein a part of the active ingredient is released in an immediate release manner and another part of is released in a sustained release manner, can be manufactured by assembling active ingredient containing layers having immediate release properties and active ingredient containing layers having sustained release properties. In a similar manner solid pharmaceutical administration forms with different active ingredients can be provided by successively creating layers comprising different active ingredients, wherein the different active ingredients are present as a mixture in the active ingredient containing layer and/or wherein the different active ingredients is present in different active ingredient containing layers. The latter is preferred if the active ingredients are incompatible to each other.

The source of irradiation used in the process can be infrared energy (IR), near-infrared energy (NIR), visible light (VIS), ultraviolet light (UV), microwave or X-radiation. Infrared energy is preferred. The source of irradiation used in the process can be diffuse (e.g. lamps, gas discharge tubes) or focused (e.g. lasers). Therefore, the invention is further directed to a process that is characterized in that the irradiation is infrared energy (IR), near-infrared energy (NIR), visible light (VIS), ultraviolet light (UV), microwave or X-radiation, preferably infrared energy (IR).

Beside active ingredient and fusible material described above the powder used in the process of the invention can comprise further materials that may be necessary for the manufacture of a solid pharmaceutical administration form that fulfill the demands that are made on them such as release properties of the active ingredient and storage stability of the solid pharmaceutical administration form. Such materials include inert material or an additional functional material.

As used herein, "inert material" refers to any material that has a melting or glass transition temperature sufficiently above the temperature that is achieved at running the process so that the shape of the inert material is remained during conducting of the process of the invention. When used in the process of the present invention the inert material provides structure to the solid pharmaceutical dosage form upon melting and fusing of the fusible material, or other useful properties such as improved powder flowability, improved disintegration or dissolution of the solid pharmaceutical application form. Examples of an inert material that may be used in the process of the present inventions are silica, silicate minerals, sugars, starches, calcium carbonate, cellulose derivatives.

As used herein, "additional functional material" refers to any material that provides a function desired to be implemented into the solid pharmaceutical dosage form e.g. to control release profile of active ingredient. For example, release profile could be delayed by hydrophobic material, which may act as diffusion barrier, by reducing wetting, or delaying disintegration. Another example of an additional functional material is a material that provides a functional coating around a core containing the API (e.g. enteric, taste-masking, moisture protective, oxygen protective). This coating may be more protective than a classical capsule (which is made of two parts and thus includes a slit).

In principle, the powder bed and/or the individual powder layer created by one spreading step is either a homogenous or an inhomogeneous mixture of a fusible material and other material, whereby upon irradiation the fusible material acts like a glue for the other material.

The structure of the solid pharmaceutical dosage form can be distinguished into voxels. As used herein, "voxel" refers to the smallest defined volume element that can be modified by the process especially by the jet printing step and the irradiation step in a regular grid in three-dimensional space. As used herein, "voxel" can refer to an individual element, which, in combination with other voxels, defines an intermediate element which is part of the three-dimensional structure. A particular voxel may be identified by x, y, and z coordinates of a selected point of geometry of the shape, such as a corner, centre, etc.

In state of the art processes all voxels belonging to a structure are completely molten in the process to allow for a homogeneous appearance, cohesiveness and physical stability of the final structure. From a biopharmaceutical perspective, a completely densified structure (i.e. coherent and non-porous) is not preferred for a solid pharmaceutical dosage form as it impairs the disintegration of the solid pharmaceutical dosage for and the dissolution of the active ingredient. In common pharmaceutical processes this problem is solved by the creation of porous materials, e.g. by granulation or tableting. However, such techniques are not transferable to 3 D printing processes and remain to be an obstacle for using such processes for the manufacture of solid pharmaceutical dosage forms.

Advantageously the process of the present invention allows to address this problem and to provide a solid pharmaceutical dosage forms that meets the requirements such as an appropriate dissolution of active ingredient or disintegration. Basis for this is that the process of the present invention allows the precise creation of well-defined voxels with different properties in terms of solubility, swelling and mechanical stability.

The process of the present invention allows the manufacture or solid pharmaceutical dosage forms with specific structures that and thereby to control the bioavailability of the active ingredient. It is well-known that the amorphous or crystalline state or the ad/absorption of an active ingredient greatly influences its bioavailability. For example, solubilized and active ingredient (e.g. with organic solvents) can be jet printed on a powder base containing suitable inert or fusible particles which interact with the active ingredient in a desired manner, thereby e.g. preventing crystallization during evaporation of the solvent/dispersing agent.

The invention is illustrated in the Figures.

Figure 1:
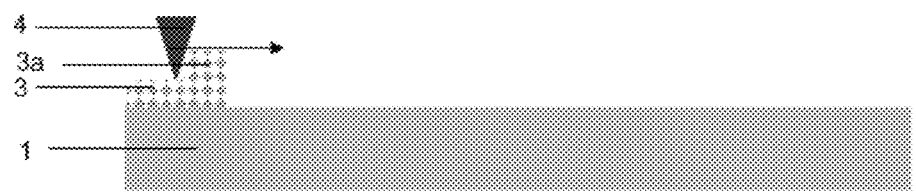

FIG. 1 illustrate the spreading step (a) of the process. Onto a mounting plate (1) a powder provided by a powder reservoir (3a) is spread by moving a doctor blade (4) in the direction indicated by an arrow to achieve a powder layer. A part of the powder layer that is already spread is indicated by (3). By repeating of the spreading of powder on the already existing powder layer(s) as often as necessary a powder bed (2) is created.

Figure 2:
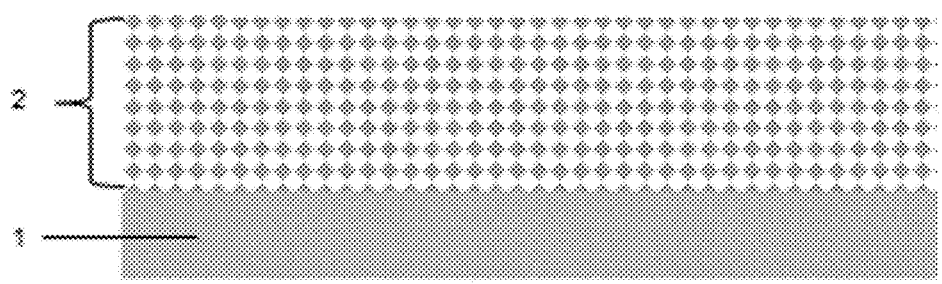

FIG. 2 shows the powder bed (2) that is created by step (b) on the mounting plate.

Figure 3:
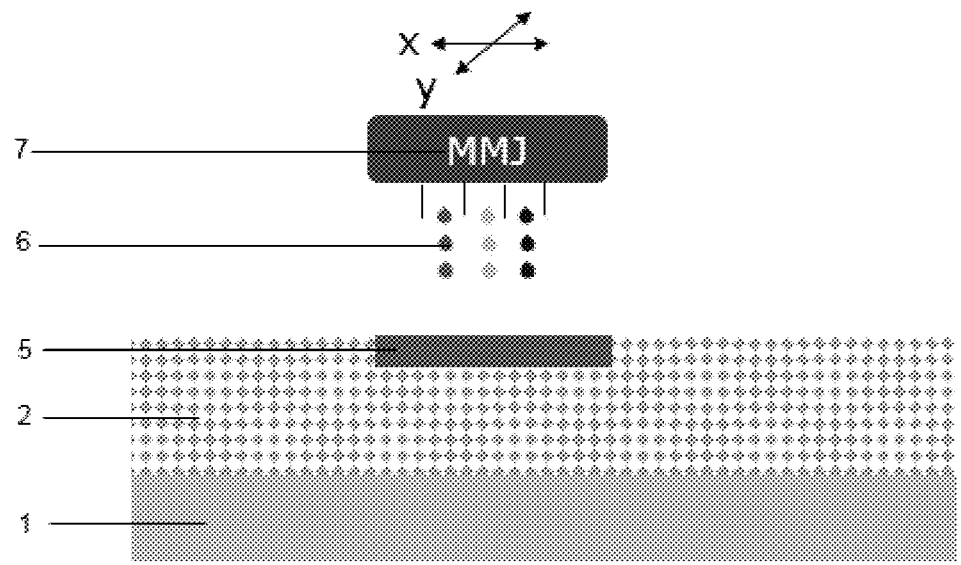

FIG. 3 shows jet printing in accordance to step (b) of the process. A multi material jet (MMJ) (7) is moved along x and/or y axis thereby jet printing a fluid (6) (in fine droplets) onto the powder bed (2). Such jet printing results in powder soaked with fluid (5) created by voxels that are adjacent to one another. As indicated by the different colors of the fluid droplets more than one fluid can be jet printed by the MMJ (7) depending on the process.

Figure 4:
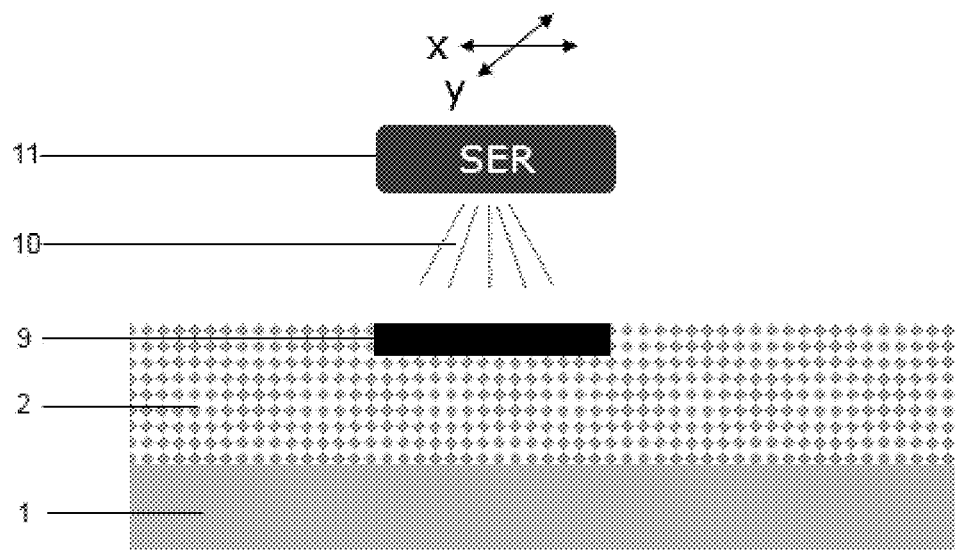

FIG. 4 shows the irradiation in accordance to step (c). A source of radiation (SER) (11) is moved along x and/or y axis above the powder soaked with fluid (5). Upon irradiation (10) by the SER the fusible material present in the powder soaked with fluid fuses thereby creating a layer of fused powder (9).

Figure 5:
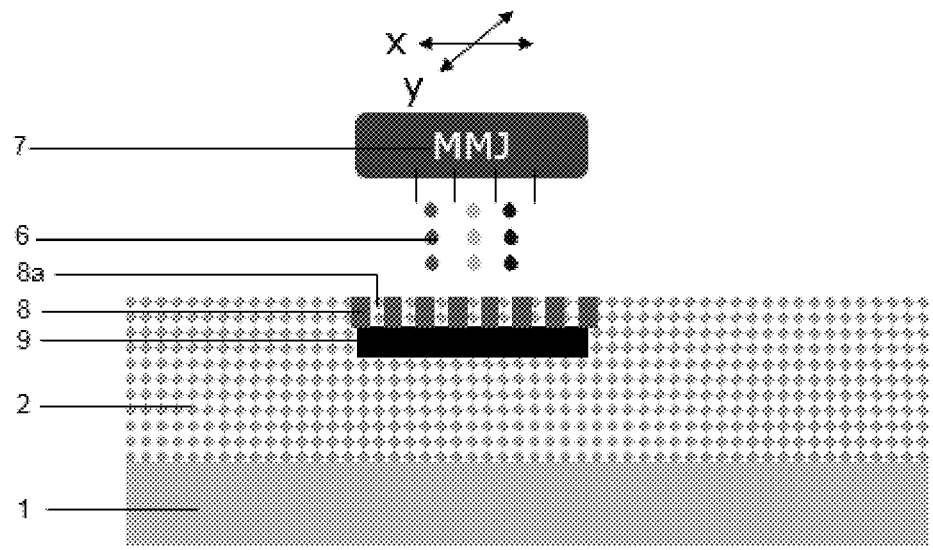

FIG. 5 shows the jet printing step as in FIG. 3 whereby the intermediate product shown in FIG. 4, onto which a layer of powder was spread, is used. In contrast to FIG. 3 the fluid is not jet printed on a continuous area but on defined areas of the powder that are delimited from each other so that a layer of powder voxels soaked with fluid (8) and powder voxels without fluid (8a) are created.

FIG. 6 shows irradiation as in FIG. 4 whereby the intermediate product shown in FIG. 5 is irradiated. Upon irradiation (10) by the SER the fusible material present in the powder voxels soaked with fluid (8) is fused thereby creating fused powder voxels (12) with adjacent unfused powder voxels. The fused powder voxels (12) are also fused with the layer with the fused powder (9) thereby forming a mechanical stable three-dimensional structure.

Depending on the desired structure of the solid pharmaceutical dosage form further layers can be added that may be completely fused powder layer (9) or a layer comprising powder voxels that are fused (12), unfused (12a) or partially fused (13). The voxels can be widely varied in their three-dimensional structure, such as their form and size, for example by adaption of the fluid composition and precise control of the jet printing (e.g. amount of fluid, fluid droplet size or placement of fluid droplet), and their distribution in an individual layer (created by subsequent performing of steps (a), (b) and (c)) and/or in the three-dimension network of the solid pharmaceutical dosage form.

Porous structures where only a part of the voxels are molten and densified can be created. While the molten voxels ensure cohesiveness of the structure suitable for filling, handling, transportation of the solid pharmaceutical dosage form without deformation or wear of friction the unmolten voxels support the disintegration upon contact with fluids (e.g. gastric, intestinal, water) by creating pores and channels for the fluid to penetrate the structure and create a larger surface for dissolution.

An example of such a structure is shown in FIG. 6 B, which is a hybrid of unsolidified powder voxels and fused powder voxels. While the fused (solidified) voxel (9) provide mechanical stability the powder the unfused powder voxels (12a) can freely dissolve.

FIG. 6 A shows another embodiment of this principle. In this embodiment unfused powder voxels (12a) are surrounded by fused voxels (12) that provide envelopment of the unfused powder voxels and mechanical stability. In this case, only the outer layer of the solid pharmaceutical dosage form is densified, while the core still consists of loose powder, thereby creating something similar to a powder-filled capsule.

FIG. 6 C shows an embodiment of another principle. In this case, all voxels of a structure are treated in the same way, thus creating a structure which would be homogeneous on a macroscopic scale, but somewhat heterogeneous on a microscopic scale. This can be achieved by fine tuning the energy exposure of a given voxel to achieve a voxel temperature close to the melt or glass transition temperature of the powder, e.g. by choosing a suitable amount of applied energy or applied energy absorber, in such a way that only a partial melting would be induced. This would result in a continuous molten and densified phase which contains unmolten particulates as microscopic defects in an otherwise continuous structure.

A more robust process is achieved by premixing two or more components with different melt or glass transition temperatures. In this case the temperature of a voxel does not need to be fine-tuned but controlled in a way that one component would melt, while another component would remain as unmolten particulates, again creating microscopic defects beneficial for disintegration and dissolution.

The process of the invention provides high flexibility how the materials that constitute the solid pharmaceutical dosage form are applied to each other. In fact, the materials can be applied either as part of the powder that is introduced by the spreading step or as part of a fluid that is jet printed to the powder. In the following examples of advantageous embodiments of the inventions are illustrated wherein the materials are applied in different ways.

FIG. 7 A shows an embodiment of the process, wherein the powder used in step (a) comprises an active ingredient (15), an inert material (16) and a fusible material (17) and the fluid used in step (b) comprises an energy absorbing material (14). FIG. 7 B shows the same embodiment of the process as in 7 A, wherein the powder does not contain an inert material (16).

FIGS. 8 A and B show embodiments of the process, wherein the powder used in step (a) comprises an active ingredient (15) and an inert material (16). In FIG. 8 A shows an embodiment of the process, wherein the energy absorbing material (14) and a fusible material (17) are present in separate fluids that are jet printed in parallel, whereas in FIG. 8 B shows an embodiment where the absorbing material (14) and a fusible material (17) are present in and jet printed as one fluid.

FIG. 9 shows an embodiment of the process, wherein the powder used in step (a) comprises an inert material (16) and a fusible material (17) and wherein a fluid comprising an energy absorbing material (14) and a fluid comprising an active ingredient are jet printed in parallel. This embodiment is especially suitable if a high precision is needed (e.g. highly potent active ingredient is used) and may also be useful to impregnate porous materials with (amorphous) active ingredient, e.g. mesoporous silica. The energy absorbing material and the active ingredient may also be contained in the same fluid.

FIGS. 10 A to D are directed to embodiments of the process wherein the powder used in step (a) comprises an inert material (16), a fusible material (17) is not included. Instead jet a fusible material (17) is printed together with an active ingredient (15) and an energy absorbing material (14) either in one fluid or in different fluids in parallel through separate channels. This embodiment combines the formation of in situ solid dispersions (either due to melting, or due to co-precipitation of polymer and API in a spray-drying like process) with melt granulation/drug product manufacturing.

FIG. 10 A shows an embodiment of the process wherein an energy absorbing material (14), an active ingredient (15) and a fusible material (17) are present in separate fluids that are jet printed in parallel.

FIG. 10 B shows an embodiment of the process wherein an energy absorbing material (14) and an active ingredient (15) are present in one fluid and a fusible material (17) is present in another fluid and wherein both fluids are jet printed in parallel.

FIG. 10 C shows an embodiment of the process wherein an energy absorbing material (14), an active ingredient (15) and a fusible material (17) are present in and jet printed as one fluid.

FIG. 10 D shows an embodiment of the process wherein a fusible material (17) and an active ingredient (15) are present in one fluid and an energy absorbing material is present in another fluid and wherein both fluids are jet printed in parallel.

FIGS. 11 A to D are directed to embodiments of the process that do not use an energy absorbing material. In such embodiments fusing takes place only in spots where the fusible material is jet printed.

FIG. 11 A shows an embodiment of the process wherein the powder used in step (a) comprises an active ingredient (15) and an inert material (16) and the fluid used in step (b) comprises a fusible material (17).

FIG. 11 B shows an embodiment of the process wherein the powder used in step (a) comprises an active ingredient (15) and the fluid used in step (b) comprises a fusible material (17).

FIG. 11 C shows an embodiment of the process wherein the powder used in step (a) comprises an inert material (16) and wherein a fluid comprising a fusible material (17) and a fluid comprising an active ingredient (15) are jet printed in parallel.

FIG. 11 D shows an embodiment of the process wherein the powder used in step (a) comprises an inert material (16) and wherein a fluid comprising a fusible material (17) and an active ingredient (15) are jet printed.

Figure 12:
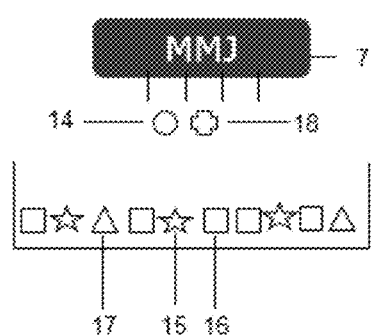

FIG. 12 shows an embodiment of the process where an additional functional material (18) is used. In such embodiment the powder used in step (a) comprises an active ingredient (15), an inert material (16) and a fusible material (17) and separate fluids comprising either an energy absorbing material (14) or an additional functional material (18) are jet printed in parallel.

The invention claimed is:

1. A process for manufacturing a solid pharmaceutical administration form comprising an active ingredient comprising the steps
   (a) spreading a powder comprising an active ingredient and a fusible material across a manufacturing area to create a powder bed;
   (c) irradiating the powder to induce melting and fusing of the fusible material present in the powder;
   (d) spreading another layer of the powder onto the surface of unfused and fused powder and subsequently performing step (c) again;
   (e) optionally repeating step (d) one or more times to build up the solid pharmaceutical administration form;
   (f) separating the solid pharmaceutical administration form from the powder bed.

2. The process according to claim 1, wherein pre-heating is applied in steps (a) and (d) prior to or after spreading the powder.

3. The process according to claim 1, wherein a cooling step is introduced between steps (e) and (f).

4. The process according to claim 1, wherein the irradiation energy is infrared energy (IR), near-infrared energy (NIR), visible light (VIS), ultraviolet light (UV), microwave or X-radiation.

5. The process according to claim 1, wherein the powder in step (a) further comprises an inert material.

6. The process according to claim 1, wherein the powder in step (a) further comprises an additional functional material.

7. The process according to claim 1, wherein the irradiating is with irradiation energy that is infrared energy (IR).

* * * * *